(12) United States Patent
Sinha et al.

(10) Patent No.: US 9,404,890 B2
(45) Date of Patent: Aug. 2, 2016

(54) METHOD FOR NONINVASIVE DETERMINATION OF ACOUSTIC PROPERTIES OF FLUIDS INSIDE PIPES

(75) Inventors: Dipen N. Sinha, Los Alamos, NM (US); Curtis F. Osterhoudt, Los Alamos, NM (US); Anirban Chaudhuri, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 962 days.

(21) Appl. No.: 13/226,444

(22) Filed: Sep. 6, 2011

(65) Prior Publication Data
US 2012/0055253 A1 Mar. 8, 2012

Related U.S. Application Data

(60) Provisional application No. 61/379,898, filed on Sep. 30, 2010.

(51) Int. Cl.
*G01N 29/024* (2006.01)
*G01N 29/34* (2006.01)

(52) U.S. Cl.
CPC ............ *G01N 29/024* (2013.01); *G01N 29/348* (2013.01); *G01N 2291/0224* (2013.01); *G01N 2291/102* (2013.01)

(58) Field of Classification Search
CPC ..... G01N 29/00; G01N 29/34; G01N 29/024; G01N 29/348; G01F 1/66
USPC ............. 702/12, 27, 50, 100; 73/12.08, 1.57, 73/592, 49.1, 622, 61.41–61.79, 64.53, 73/861.25, 861.31
See application file for complete search history.

(56) References Cited

U.S. PATENT DOCUMENTS

| | | | |
|---|---|---|---|
| 6,644,119 B1 * | 11/2003 | Sinha | 73/579 |
| 6,931,945 B2 * | 8/2005 | Takeda et al. | 73/861.25 |
| 7,260,482 B2 * | 8/2007 | Volker et al. | 702/22 |
| 7,775,086 B2 | 8/2010 | Jesse et al. | |
| 2001/0039830 A1 * | 11/2001 | Hastings et al. | 73/54.41 |

(Continued)

OTHER PUBLICATIONS

U.S. Appl. No. 13/225,734, "Integrated Acoustic Phase Separator and Multiphase Fluid Composition Monitoring Apparatus and Method," by Dipen N. Sinha, filed Sep. 6, 2011.

(Continued)

*Primary Examiner* — Manuel Rivera Vargas
(74) *Attorney, Agent, or Firm* — Samuel M. Freund; Cochran Freund & Young, LLC

(57) ABSTRACT

A method for determining the composition of fluids flowing through pipes from noninvasive measurements of acoustic properties of the fluid is described. The method includes exciting a first transducer located on the external surface of the pipe through which the fluid under investigation is flowing, to generate an ultrasound chirp signal, as opposed to conventional pulses. The chirp signal is received by a second transducer disposed on the external surface of the pipe opposing the location of the first transducer, from which the transit time through the fluid is determined and the sound speed of the ultrasound in the fluid is calculated. The composition of a fluid is calculated from the sound speed therein. The fluid density may also be derived from measurements of sound attenuation. Several signal processing approaches are described for extracting the transit time information from the data with the effects of the pipe wall having been subtracted.

34 Claims, 11 Drawing Sheets

(56) References Cited

U.S. PATENT DOCUMENTS

| | | |
|---|---|---|
| 2004/0168523 A1 | 9/2004 | Fernald et al. |
| 2005/0097943 A1* | 5/2005 | Sinha .................... 73/61.49 |
| 2005/0109112 A1* | 5/2005 | Gysling et al. ............. 73/587 |
| 2005/0125166 A1 | 6/2005 | Loose et al. |
| 2005/0215902 A1 | 9/2005 | Greenwood |
| 2007/0175280 A1* | 8/2007 | Johansen .................. 73/599 |
| 2007/0293759 A1* | 12/2007 | Eilers et al. ............. 600/454 |
| 2008/0173100 A1* | 7/2008 | Davis .................... 73/861.27 |
| 2009/0078049 A1 | 3/2009 | Sinha |
| 2009/0241672 A1 | 10/2009 | Gysling |
| 2011/0271769 A1* | 11/2011 | Kippersund et al. ....... 73/861.28 |

OTHER PUBLICATIONS

U.S. Appl. No. 13/225,750, "Apparatus and Method for Noninvasive Particle Detection Using Doppler Spectroscopy," by Dipen N. Sinha, filed Sep. 6, 2011.

U.S. Appl. No. 13/226,209, "Multiphase Fluid Characterization System," by Dipen N. Sinha, filed Sep. 6, 2011.

International Search Report, International Searching Authority, Jan. 4, 2012, pp. 1-13.

* cited by examiner

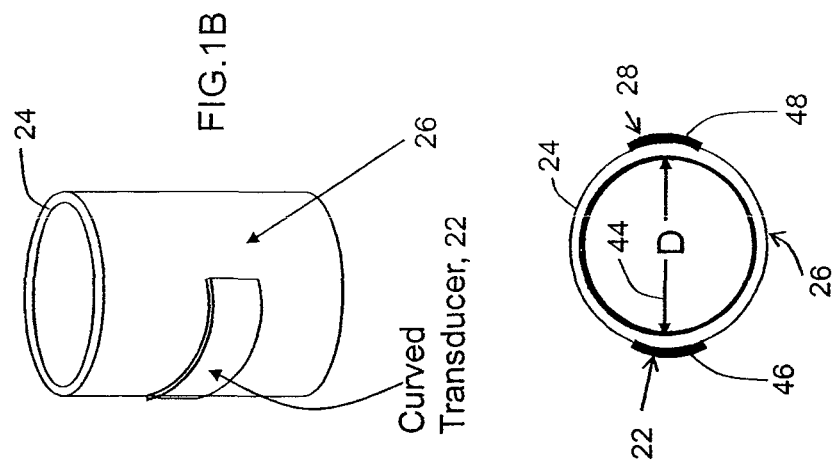
FIG. 1B
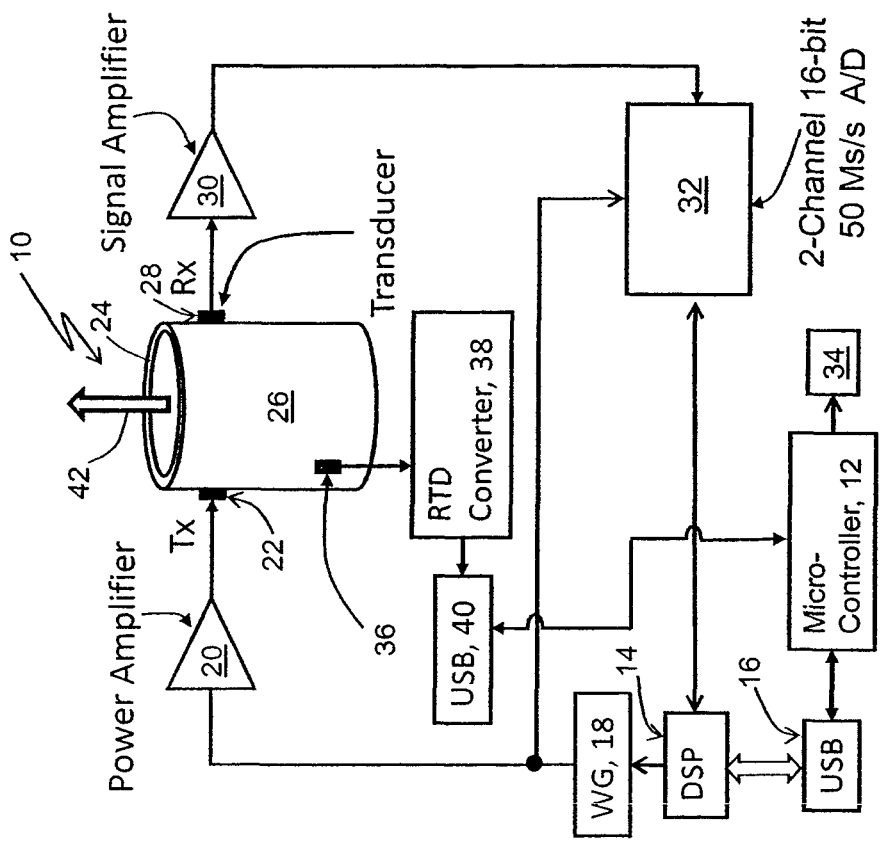
FIG. 1C
FIG. 1A

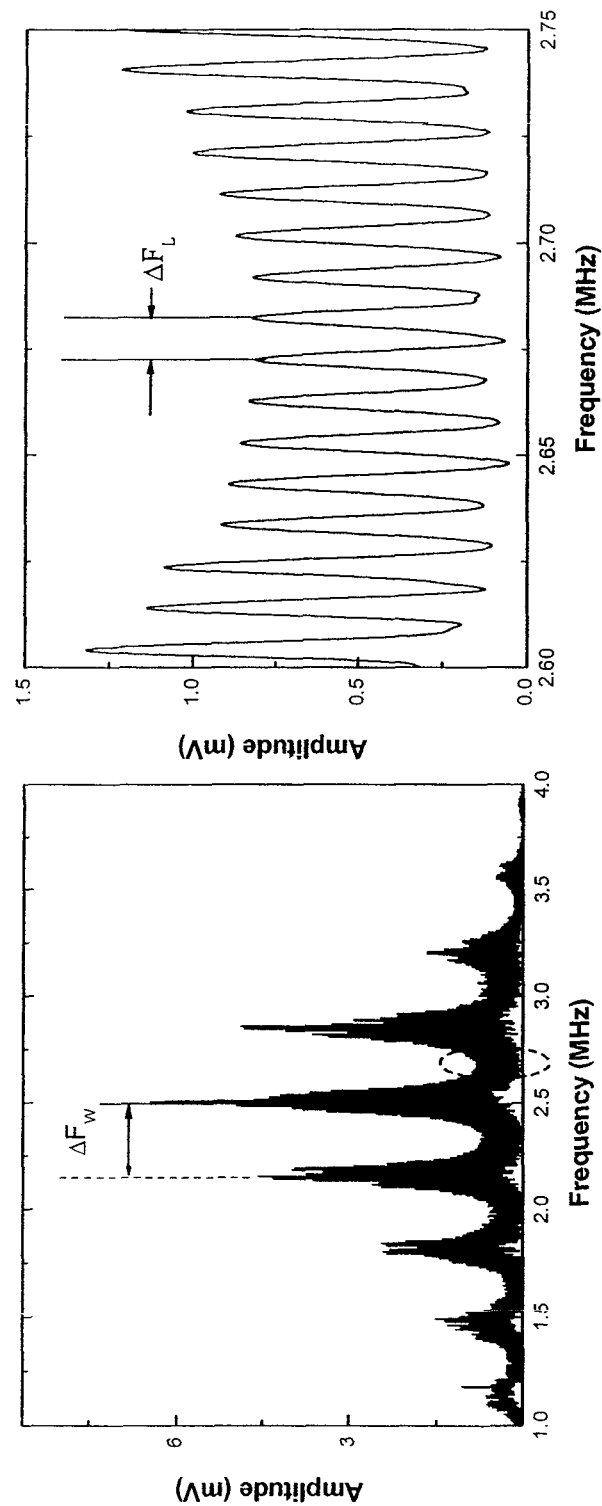

METHOD FOR NONINVASIVE DETERMINATION OF ACOUSTIC PROPERTIES OF FLUIDS INSIDE PIPES

CROSS-REFERENCE TO RELATED APPLICATIONS

The present application claims the benefit of U.S. Provisional Patent Application No. 61/379,898 for "Method For Noninvasive Determination Of Acoustic Properties Of Fluids Inside Pipes" which was filed on Sep. 3, 2010, the entire contents of which is hereby specifically incorporated by reference herein for all that it discloses and teaches.

STATEMENT REGARDING FEDERAL RIGHTS

This invention was made with government support under Contract No. DE-AC52-06NA25396 awarded by the U.S. Department of Energy. The government has certain rights in the invention.

FIELD OF THE INVENTION

The present invention relates generally to a method for determining the composition of fluids flowing through pipes and, more particularly, to a method for noninvasively determining sound speed and sound attenuation of fluids flowing through thick-walled pipes and conduits for determining the composition of the fluid.

BACKGROUND OF THE INVENTION

The determination of the acoustic properties of fluids in containers or flowing through conduits and pipes is important In many industries, in particular in oil production, as these properties may be used to determine fluid composition. Typically, acoustic measurements (for example, sound speed and sound absorption in liquids) are made with sensors attached to the pipe through special windows machined into the pipe wall where the sensor elements make physical contact with the fluid or are mounted directly in the fluid. In such situations, the sensors or the windows are subject to fouling by the fluid, making long-term operation and maintenance difficult. Moreover, if a sensor is placed inside the fluid or intrudes into the liquid through the wall, it can affect the flow pattern and contaminate the measurements that are sensitive to a disruption of the flow pattern.

High voltage pulsed signals having 10 μm is duration have been used to excite sound waves in an ultrasonic transducer attached to a curved delay line that conforms to the exterior curvature of a pipe, the sound waves being detected by a second transducer after traversing through the fluid in the pipe. The transit time of the pulses is measured by threshold detection of the received signal, which is difficult due to multiple reflections in the container wall and also due to propagation of sound through the wall itself. The average of 100 signals is required for proper threshold detection for a transit time measurement from which fluid sound speed and subsequently fluid composition are determined.

SUMMARY OF THE INVENTION

Embodiments of the present invention overcome the disadvantages and limitations of the prior art by providing a noninvasive method for determining the composition of a fluid inside a pipe.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein the method for noninvasively determining the composition of a multiphase fluid comprising oil and water flowing through pipe having a wall and an outside surface, hereof, including: generating an ultrasonic frequency chirp signal using a transmitting transducer in ultrasonic communication with the outside surface of the pipe; receiving the generated frequency chirp signal on a receiving transducer in ultrasonic communication with the outside surface of the pipe diametrically opposed to the transmitting transducer after the chirp signal passes through said multiphase fluid, wherein an electrical signal is generated in response thereto; receiving the electrical signal; dechirping the frequency chirp by multiplying the received signal and the generated frequency chirp signal and obtaining the difference frequency from which the total transit time of the frequency chirp signal is determined; determining the time delay of the frequency chirp signal in the wall of the pipe; and subtracting the time delay from the total transit time to determine the propagation time of the frequency chirp signal through the multiphase fluid, from which the composition of the multiphase fluid is determined.

In another aspect of the present invention and in accordance with its objects and purposes, the method for noninvasively determining the composition of a multiphase fluid comprising oil and water flowing through pipe having a wall and an outside surface, hereof, includes: generating an ultrasonic frequency chirp signal using a transmitting transducer in ultrasonic communication with the outside surface of the pipe; receiving the generated frequency chirp signal on a receiving transducer in ultrasonic communication with the outside surface of the pipe diametrically opposed to the transmitting transducer after the chirp signal passes through the multiphase fluid, wherein an electrical signal is generated in response thereto; receiving the electrical signal; cross-correlating the transmitted signal with the received signal, wherein cross-correlation peaks are generated; selecting the highest peak which corresponds to the total transmit time of the frequency chirp signal; determining the time delay of the frequency chirp signal in the wall of the pipe; and subtracting the time delay from the total transit time to determine the propagation time of the frequency chirp signal through said multiphase fluid, from which the composition of said multiphase fluid is determined.

In yet another aspect of the present invention and in accordance with its objects and purposes, the method for noninvasively determining the composition of a multiphase fluid comprising oil and water flowing through pipe having a wall, an outside surface, and an axis, hereof, includes: generating an ultrasonic frequency chirp signal using a transmitting transducer in ultrasonic communication with the outside surface of the pipe; receiving the generated frequency chirp signal on a receiving transducer in ultrasonic communication with the outside surface of the pipe diametrically opposed to the transmitting transducer after the chirp signal passes through the multiphase fluid, wherein an electrical signal is generated in response thereto; receiving the electrical signal; cross-correlating the transmitted signal with the received signal, wherein cross-correlation peaks are generated; determining the time between consecutive peaks, wherein the determined time is twice the travel time through the multiphase fluid, from which the composition of the multiphase fluid is determined.

In still another aspect of the present invention and in accordance with its objects and purposes, the method for noninvasively determining the composition of a multiphase fluid comprising oil and water flowing through pipe having a wall and an outside surface, hereof, includes: generating an ultrasonic frequency chirp signal having a duration shorter than the time the frequency chirp takes to pass through the multiphase fluid using a transmitting transducer in ultrasonic communication with the outside surface of the pipe; receiving the generated frequency chirp signal on a receiving transducer in ultrasonic communication with the outside surface of the pipe diametrically opposed to the transmitting transducer after the chirp signal passes through the multiphase fluid, wherein an electrical signal is generated in response thereto; receiving the electrical signal; transforming the electrical signal using a Short Time Fourier Transform, whereby a plot of the frequency variation of the received frequency chirp as a function of time is generated, amplitude modulations due to wall resonances appear as individual data points; and the generated frequency chirp is a straight line having a slope; performing a least-squares fit of the data points with a straight line having the slope; determining the intercept on the time axis from which the total transit time is determined; determining the time delay of the frequency chirp signal in the wall of the pipe; and subtracting the time delay from the total transit time to determine the propagation time of the frequency chirp signal through the multiphase fluid, from which the composition of the multiphase fluid is determined.

Benefits and advantages of embodiments of the present invention include, but are not limited to, providing a noninvasive method for determining the composition of a fluid that can either be flowing or static inside a pipe while taking advantage of the pipe walls to assist the measurement rather than adversely effecting the measurement. Other benefits include high-quality composition determinations unaffected by the presence of the wall of the container or pipe, high signal-to-noise ratio of the due to the use of a frequency chirp and methods for signal analysis that simultaneously use multiple methods for determining the sound speed in the fluid and are superior to conventional pulse time-of-flight methods, extraction of high-quality sound speed data even when the excitation chirp signal is not of high quality and may be square-wave based which simplifies the wave generation and allows lower power consumption electronics to be used.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of an embodiment of the measurement apparatus of the present invention effective for practicing the method hereof, FIG. 1B is a schematic representation of a perspective view of a pipe and a curved transducer affixed to the exterior surface thereof, and FIG. 1C is a schematic representation of a top view of the pipe and curved transducers.

FIG. 4A illustrates a generated chirp input signal, s(t), shown as a line which propagates through a system and is detected by a receiver after a certain delay, the delayed chirp signal being $s(t-\tau)$ such that in a linear system is linear, the two signals are parallel lines and the delay time, $\tau$, is the sought transit time measurement, while FIG. 4B illustrates that the measurement may also be considered as the shift in frequency between the two chirp lines given by $\Delta f$, which is a fixed frequency, this difference frequency, $s_{diff}(t)$, called the de-chirped frequency, being constant during the period of overlap of the two signals, and equivalent to the delay time.

FIG. 6A is a graph of the signal detected by the receiver transducer from a water-filled brass pipe, while FIG. 6B is a graph of the cross-correlation of this signal with the source signal from the transmitter transducer illustrating significant pulse compression.

FIGS. 7A and 7B are graphs showing the first chirp burst received by the receiver transducer without multiple echoes for a stainless steel and a brass pipe having identical dimensions, respectively, while

FIG. 9A shows the Fast Fourier Transform of received chirp signals, over a sufficient time period that effects due to recording multiple echoes for a brass pipe filled with water can be separated, as in FIG. 8D hereof, with a portion of the graph around 2.7 MHz being enclosed by a dashed oval curve, while FIG. 9B shows an expanded view of the emphasized portion of FIG. 9A illustrating the Fast Fourier Transform of peaks observed in the fluid between the two pipe walls.

FIG. 11A is a graph of the Joint Time-Frequency Analysis of the product of the transmitted chirp and the received delayed chirp (FIGS. 4A and 4B) for a brass pipe containing water, while

DETAILED DESCRIPTION OF THE INVENTION

Figure 2:
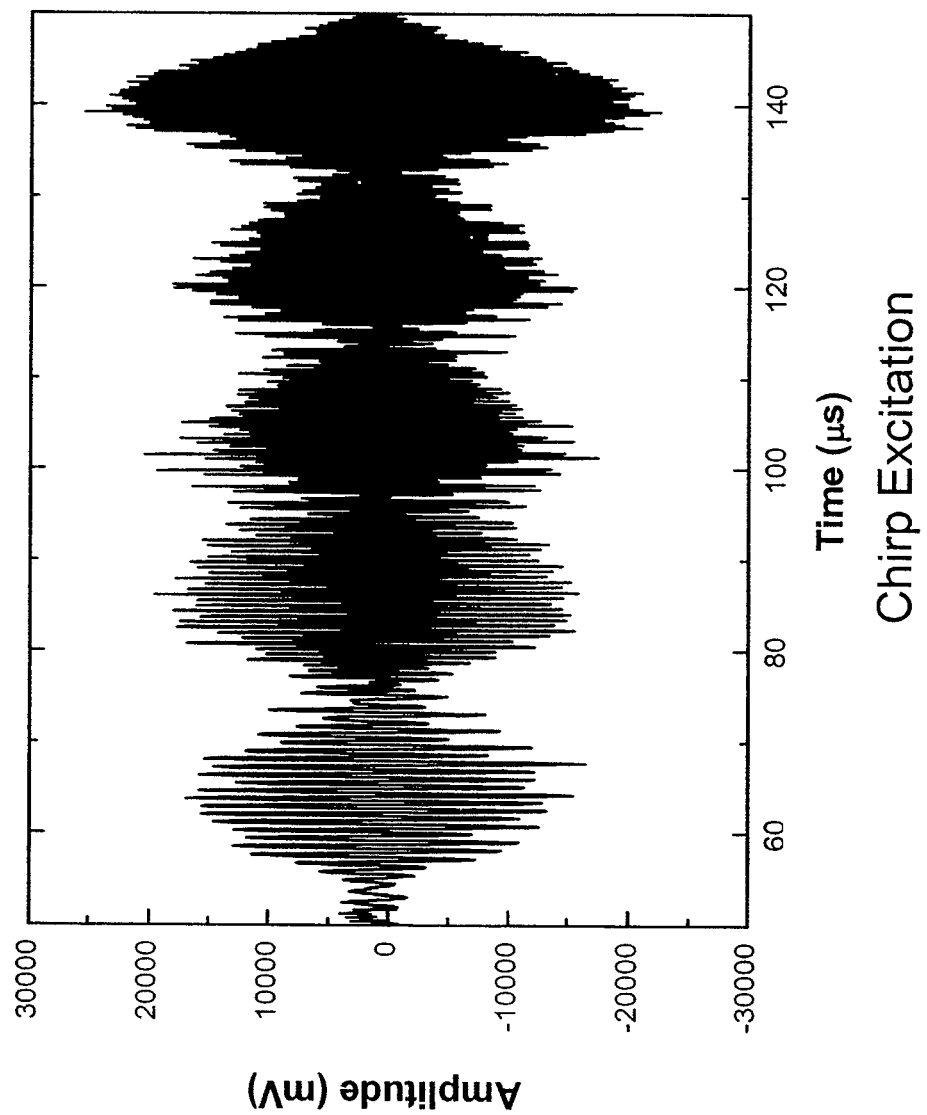
FIG. 2 is a graph of amplitude versus time illustrating data obtained using the apparatus shown in FIGS. 1A-1C, hereof, where the multiple burst characteristics are due to the transmission characteristics of the pipe wall.

Briefly, an embodiment of the present invention includes a method for noninvasively determining the composition of a fluid inside a pipe. The method includes exciting a first transducer located on the external surface of the pipe through which the fluid under investigation is flowing, to generate an ultrasound chirp signal, as opposed to conventional pulses. The chirp signal is received by a second transducer disposed on the external surface of the pipe opposing the location of the first transducer, from which the transit time through the fluid is determined and the sound speed of the ultrasound in the fluid is calculated. The composition of a fluid is calculated from the sound speed therein. The fluid density may also be derived from measurements of the sound attenuation.

Chirp measurements permit high signal-to-noise ratios to be obtained, and lower power operation. The transducers may be directly attached to the pipe, and the transducer surface may have the same radius of curvature as the pipe. Such curved transducers do not require delay lines to obtain adequate signals. A digital signal processor (DSP) circuit may be used process the received chirp signal to provide the sound speed. The use of high dynamic-range (16-bit) digitizers to record the received signal simplifies the measurements by not requiring amplifier again adjustment as the attenuation of the fluid flowing through the pipe changes.

Embodiments of the present method can provide accurate transit time determinations that are not affected by the presence of a thick pipe wall, and may advantageously use the wall. The transit time through the wall is determined simultaneously with the transit time in the fluid inside the pipe or container. Additionally, the curved transducers may mitigate the generation of guided wave modes through the pipe wall by suppressing the generation of such wave modes. Signal analysis procedures described in detail hereinbelow provide a robust transit time measurement which is not affected by random noise.

The received signal propagates through both the wall of the pipe and the fluid inside the pipe. In a system where the fluid is flowing and also contains gas, the signal can be rather noisy and it is not possible to determine the transit time by a simple threshold detection as conventionally done. In accordance with embodiments of the present invention, five signal processing approaches may be used to extract the transit time information from the data with pipe wall effects having been subtracted. These signal analysis techniques include: (1) Joint Time-Frequency Analysis to obtain the propagation delay of each point of the chirp; (2) a de-chirping technique for providing a fixed frequency signal that is directly related to the chirp delay; (3) a cross-correlation technique that determines the transit time through the fluid and the multiple reflections through the fluid, and that provides sound attenuation information; (4) Fast Fourier transformation (FFT) of the received signal to obtain the interference spectrum of the sound signal in the fluid and in turn its sound speed; and (5) an FFT of the received signal to obtain the signal transmission through the wall and the wall resonance peaks that may be used for determining either the wall thickness or the transit time through the wall.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIG. 1A, a schematic representation of an embodiment of the measurement apparatus, 10, of the present invention effective for practicing the method hereof is illustrated. Microcontroller, 12, controls digital signal processor (DSP), 14, through universal serial bus (USB), 16. DSP 14 loads the chirp waveform into arbitrary waveform generator (WG), 18, which produces the linear chirp waveform to be directed to power amplifier, 20, for driving transmitting transducer, 22. Waveform generator 18 may generate any mathematically generated waveform and is not limited to producing linear frequency chirp. The chirp signal typically used is sinusoidal, but a square wave chirp can be used as well to reduce power consumption by the output amplifier and can also simplify the amplifier design. However, a square wave chirp signal produces higher harmonics that can affect the measurement accuracy unless properly taken care of in the data analysis. Apparatus 10 generates signals in a frequency range between about 100 kHz and approximately 10 MHz having amplitudes between about 1 mV and about 50 V. The chirp duration may be between approximately 1 µs and about 10 ms. Transmitting transducer 22 may be differentially driven through a transformer (not shown in FIG. 1A) to avoid difficulties with ground loops. Transmitting transducer 22 is placed in ultrasonic communication with wall, 24, of pipe or tube, 26, which may include attaching transducer 22 directly to the exterior of wall 24.

Receiving transducer, 28, is disposed in ultrasonic communication, which may include direct attachment of transducer 28 to the exterior of wall 24, diametrically opposed to transmitting transducer 22. Signal generated by receiving transducer are amplified by signal amplifier, 30, having gains between approximately 10 and approximately 60 db before being digitized using 2-channel, 16-bit, 60 Mega samples/s digitizer, 32, having data storage memory. Receiver transducer 28 may be transformer coupled for providing a differential signal, which may be advantageous both for electrical safety and for reduction in ambient noise pick up. Signal amplifier 30 may be disposed on a circuit board for close positioning to transducer 28 and shielded within a metal case. The output from WG 18 may be simultaneously digitized by digitizer 32, and the two chirp signals directed to DSP 14 for analysis before displaying on screen after processing by microcontroller 12, or recorded in the memory of microcontroller 12. Thermometer element, 36, may be attached to pipe wall 24 for measuring the temperature of wall 24 during measurements. The signal from sensor 36 may be digitized by resistance temperature device (RTD) converter, 38, and directed to USB bus 40 for communication with microcontroller 12. Signals may be processed between approximately every 0.1 s and about 1 s, and stored in microcontroller 12 or displayed on screen 34. Arrow, 42, depicts direction of fluid flow in pipe 26. Additional information concerning apparatus for such analyses may be found in patent application Ser. No. 13/225,734 for "Integrated Acoustic Phase Separator And Multiphase Fluid Composition Monitoring Apparatus And Method", by Dipen N. Sinha, filed on 6 Sep. 2011, in patent application Ser. No. 13/225,750 for "Apparatus And Method For Noninvasive Particle Detection Using Doppler Spectroscopy" by Dipen N. Sinha, filed on 6 Sep. 2011, and in patent application Ser. No. 13/226,209 for "Multiphase Fluid Characterization System" by Dipen N. Sinha, filed on 6 Sep. 2011, the entire contents of said patent applications being hereby incorporated by reference herein for all that they disclose and teach.

Transducers 22 and 28 may be made from piezoelectric (PZT) material and can withstand a temperature up to 250° F. As stated hereinabove, such transducers can be shaped so as to conform to the outer radius of pipe 26. Stainless steel and brass pipes used to collect the data set forth hereinbelow had inner diameters, 44, of about 3 in. and wall 24 thicknesses of 0.25 in. Other materials may also be used. The size of each PZT element used was 1 cm×2 cm and curved along the long axis as shown in FIG. 1B, which shows a schematic representation of a perspective view of pipe 26 and curved transducer 22. FIG. 1C is a schematic representation of a top view of pipe 26 and curved transducers 22 and 28. Transducers 22 and 28 may be cemented to the exterior surface of wall 24 using high-temperature epoxy for extended use but other attachment means may also be used.

The center frequency of transducer elements 22 and 28 can vary between about 1.5 and about 5 MHz, depending on the particular application. For highly attenuating heavy oils a lower frequency is used than for fluids that have high water content for which the higher frequencies are used. For smaller pipe diameters and less attenuating fluids, the frequency can be as high as approximately 10 MHz, which is not a limitation of the electronics which can readily be modified to operate at 50 MHz. To make the PZT elements broadband, the outer sides, 46, and, 48, of each of elements 22 and 28, respectively (FIG. 1C), are covered with a layer of tungsten-loaded epoxy. Advantageously, this also makes the transducers more robust. As stated hereinabove, transducers 22 and 28 are coupled to the outer surface of pipe 26 with a thin layer of epoxy, and delay lines are not necessary. Such contact suppresses the generation of guided wave modes in the pipe wall and any complications due to the guided wave modes. As also stated hereinabove, the two transducers are positioned directly opposite of one another to obtain a strong signal, and to provide a well-defined sound beam pattern inside the pipe. Other relative transducer locations may be employed, but provide poorer signal response.

FIG. 2 is a graph of amplitude versus time illustrating data obtained using the apparatus shown in FIGS. 1A-1C hereof. The chirp duration was 100 μs, the frequency range was between approximately 1 and about 4 MHz, and the excitation voltage was less than about 10 V peak-to-peak. The measurement was made in a water-filled stainless steel pipe having 3-inch inner diameter and 0.25 inch wall thickness. The multiple burst characteristics in FIG. 2 are due to the transmission characteristics of the pipe wall as a function of frequency, and will be discussed in greater detail hereinbelow. By contrast, data obtained using previous apparatus or methods for noninvasive sound transit time measurements in pipes or containers with thick walls by applying pulses of 10 μs duration and excitation levels as high as 500 V must be averaged to obtain usable signals for determining pulse transit time based on detecting the onset of the detected burst. As stated hereinabove, such detection is prone to errors since it relies on a threshold detection which may vary with signal level, and the remainder of the burst signal beyond the onset is typically not used since it contains multiple reflections within the pipe wall.

Figure 3A:
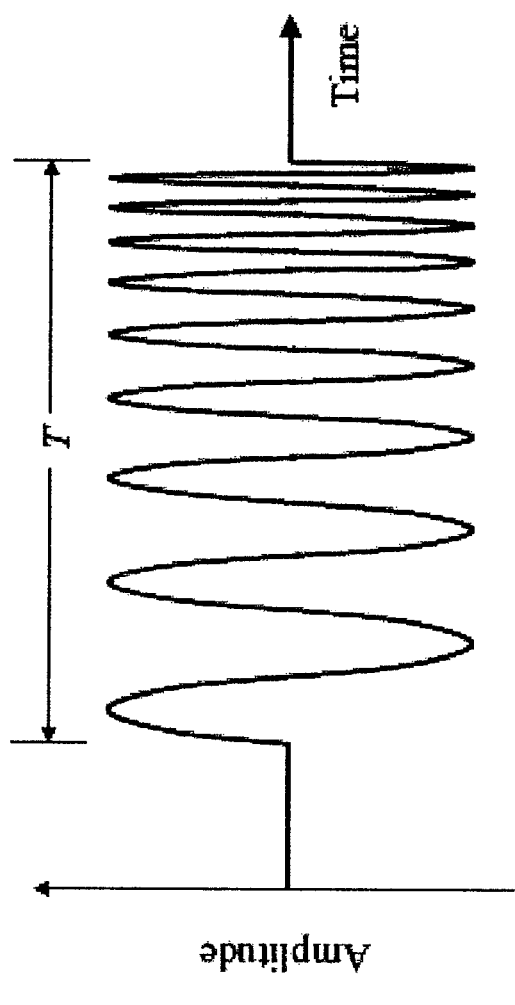
FIG. 3A illustrates a typical chirp signal commencing at a low frequency, $f_1$, which is increased to a higher frequency, $f_2$, in a continuous manner over a time period T, while the frequency variation of the chirp as a function of time is shown in FIG. 3B.
Figure 3B:
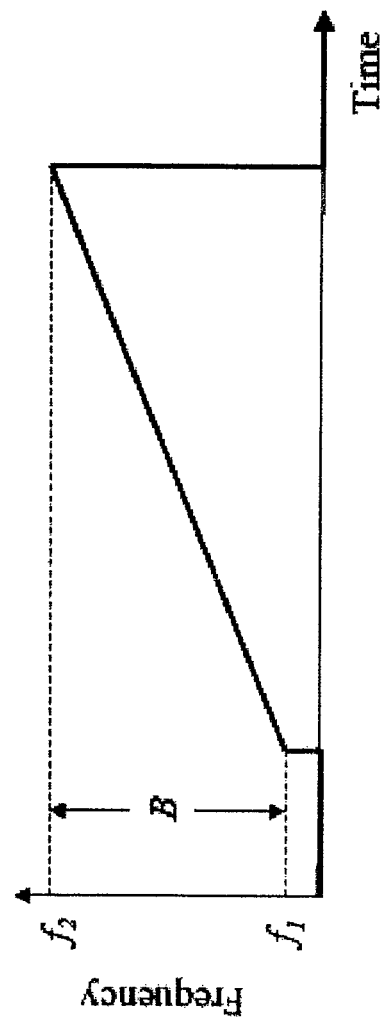

FIG. 3A illustrates a typical chirp signal. A frequency chirp ranging from about 100 kHz to approximately 10 MHz having duration between approximately 10 μs and 200 μs may be used. The duration depends on the pathlength through fluid and may be longer for larger pathlengths. The chirp signal starts at a low frequency, $f_1$, which is increased to a higher frequency, $f_2$, in a continuous manner over a time period T. The frequency variation of the chirp as a function of time is shown in FIG. 3B. The bandwidth of the chirp is $B=f_2-f_1$ and its period is T. Determining the transit time of this chirp signal through a fluid-filled pipe (or any other container) provides the relevant transit time measurement. Chirp signals have several advantages. A chirp distributes the transmitted power for the measurement over a longer time period; therefore, high voltage excitation, as used in conventional pulse measurements, is not required, and signal excitation levels less than about 10 V is sufficient for most measurements. A chirp also allows the use of pulse compression techniques for enhancing the signal-to-noise (S/N) ratio of a measurement by the pulse compression ratio=B×T. Therefore, without signal averaging, for high bandwidth, B, and longer duration, T, it is possible to obtain very high S/N, typically several orders of magnitude greater than traditional pulse measurements. Chirp measurements further permit the use of several powerful signal processing methods for transit time extraction.

Figures 4A, 4B:
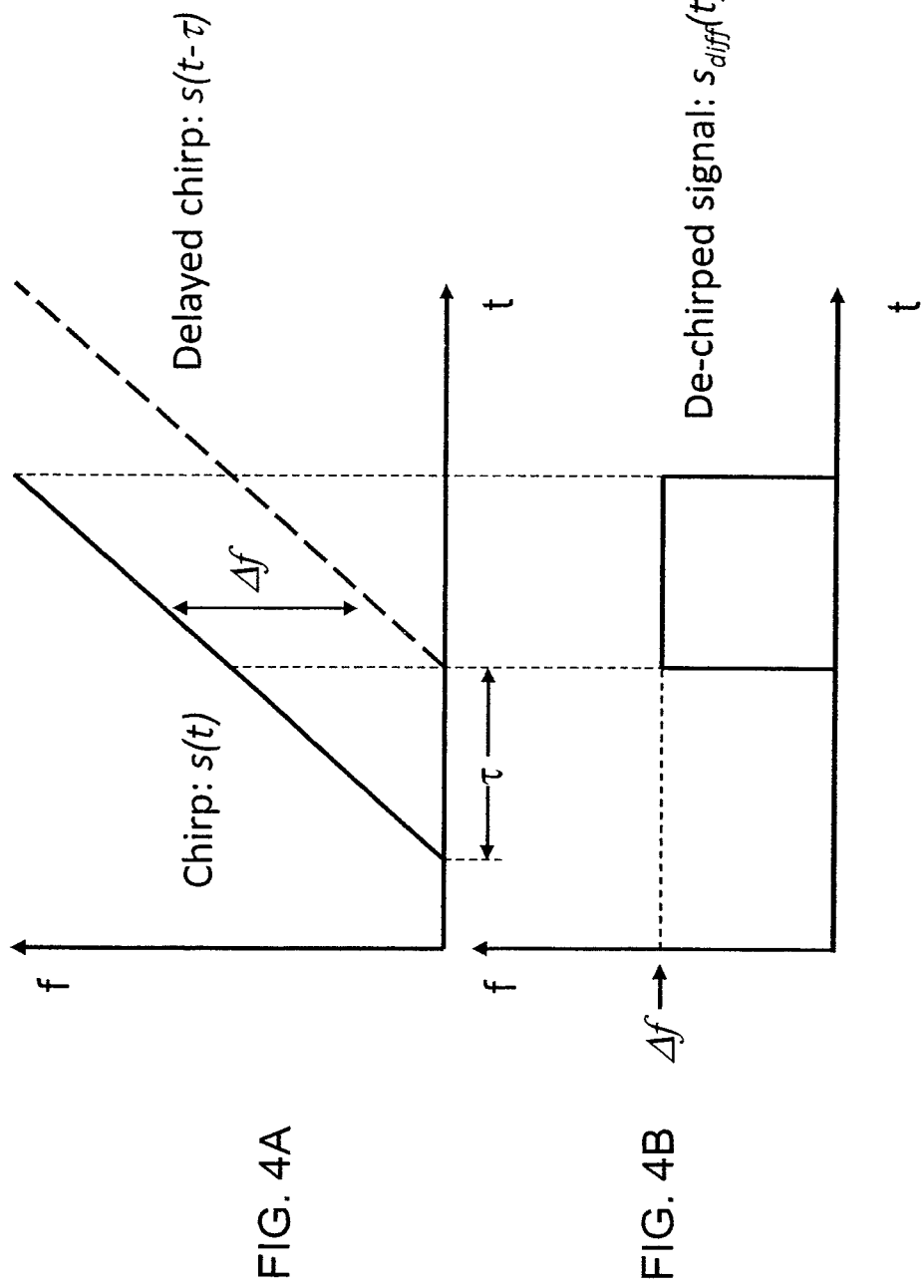

FIGS. 4A and 4B are schematic representations of chirp signal analyses. In FIG. 4A, a generated chirp input signal s(t) is shown as a line having an angle (see FIG. 3B). This signal propagates through a system (for example, a water-filled pipe) and is detected by a receiver (output) after a certain delay, the delayed chirp signal being s(t−τ). If the system is linear, the two signals are parallel lines and the delay time, τ, is the sought transit time measurement. The measurement may also be considered as the shift in frequency between the two chirp lines as given by Δf, which is a fixed frequency. This difference frequency, $s_{diff}(t)$, called the de-chirped frequency and illustrated in FIG. 4B, is a fixed frequency during the period of overlap of the two signals, and is equivalent to the delay time τ. This is because a fixed time difference between two linear chirped signals gives a fixed frequency signal as each instance of one chirp is shifted by the same amount in frequency from the other. The shift in time is thus linearly related to the shift in frequency and, therefore, a measurement of frequency shift provides a measure of time delay. An advantage is that the measurement is determined over the entire region of the frequency overlap of the two chirps and thus an averaged value is obtained. By contrast, in the widely used and traditional time-of-flight measurement using a pulse to determine time delay, a single point on the pulse is used and this becomes difficult to execute if the received pulse suffers distortion which is invariably the situation when a sound pulse propagates through a flowing fluid.

A straightforward manner for measuring the de-chirped (difference) frequency in an actual measurement is to multiply the input and output chirp signals together as described hereinbelow. The two chirp signals, sent [x(t)] and received [y(t)] following a time delay □, can be defined mathematically as:

$$x(t)=s(t)=\sin(\omega_0 t+\tfrac{1}{2}\dot{\omega}t^2) \qquad (1)$$

$$y(t)=s(t-\tau)=x(t-\tau)\cdot u(t-\tau)=\sin[\omega_0(t-\tau)+\tfrac{1}{2}\dot{\omega}(t-\tau)^2]\cdot u(t-\tau) \qquad (2)$$

where $\omega_0$ is the start frequency and T is the chirp duration. The chirp rate, $\dot{\omega}$, is equal to Δω/T, where Δω is the change in frequency during the chirp ($\omega_1-\omega_0$). The de-chirping signal z(t) is the product of Equations (1) and (2)

$$s_{diff}(t)=x(t)\cdot y(t)=\sin(\omega_0 t+\tfrac{1}{2}\dot{\omega}t^2)\cdot\sin[\omega_0(t-\tau)+\tfrac{1}{2}\dot{\omega}(t-\tau)^2]\cdot u(t-\tau), \qquad (3)$$

which can be simplified to $$s_{diff}(t)=\tfrac{1}{2}[\cos(\dot{\omega}\tau\hat{t}+\hat{\phi})-\cos\{(2\omega_0+\dot{\omega}\tau+\dot{\omega}\hat{t})\hat{t}+\hat{\phi}\}]\cdot u(\hat{t}) \qquad (4)$$

where $\hat{t}=t-\tau$. Hence, the frequency spectrum of the de-chirped signal will contain a single peak at ωτ and a linearly increasing section that starts at $2\omega_0+\dot{\omega}\tau$. Note that any additional reflections within the pipe walls will manifest as other distinct peaks at frequencies $\dot{\omega}(\tau+n\tau_d)$, where $\tau_d$ is the wall delay for each of the 'n' reflections.

The first peak frequency of the de-chirped sinusoid is proportional to τ. Therefore, the de-chirping process comprises a differential multiplication between chirp signal and delayed chirp signal, which is a frequency mixing process yielding a fixed difference frequency and a time-variant sum frequency.

The time delay, τ, between two chirp signals can be converted to a frequency signal (Δf) by the de-chirping process.

Figures 5A, 5B:
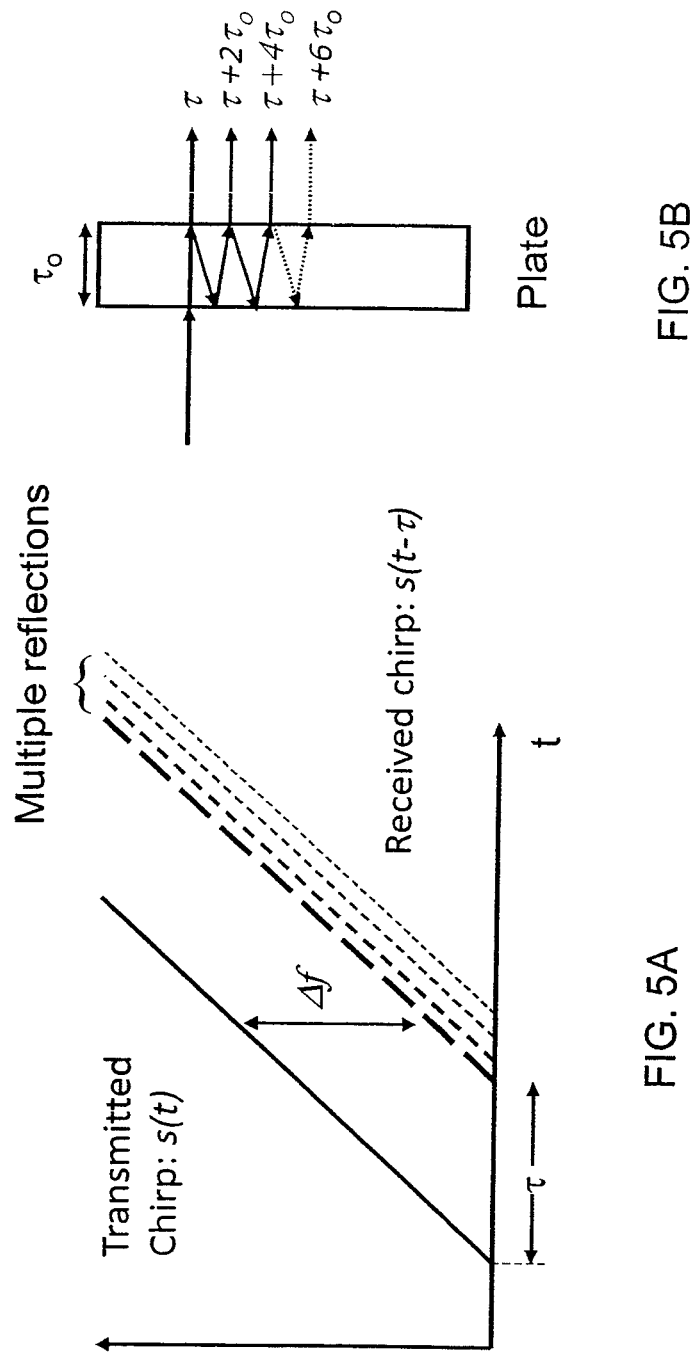
FIG. 5A shows the delayed chirp signal including a series of equally spaced chirps in time having decreasing amplitude and resulting from reflections inside the wall of the pipe or container, while FIG. 5B schematically illustrates a pulsed sound signal being multiply reflected as it traverses a wall.

FIG. 5A shows the effect of the pipe or container wall on the measurements. In this situation, the delayed chirp signal is observed with a series of equally spaced chirps in time having decreasing amplitude. FIG. 5B schematically illustrates a pulsed sound signal being multiply reflected as it traverses a wall, where only one wall is shown for illustrative purposes. The transit time through the wall is $\tau_o$ and each reflection adds an additional time delay of $2\tau_o$. Since each signal pass is affected by the acoustic impedance mismatch between the fluid and the wall material, consecutive reflections are reduced in amplitude, which includes information on fluid density if the acoustic impedance of the wall is known and from which fluid density may be determined.

Figures 6A, 6B:
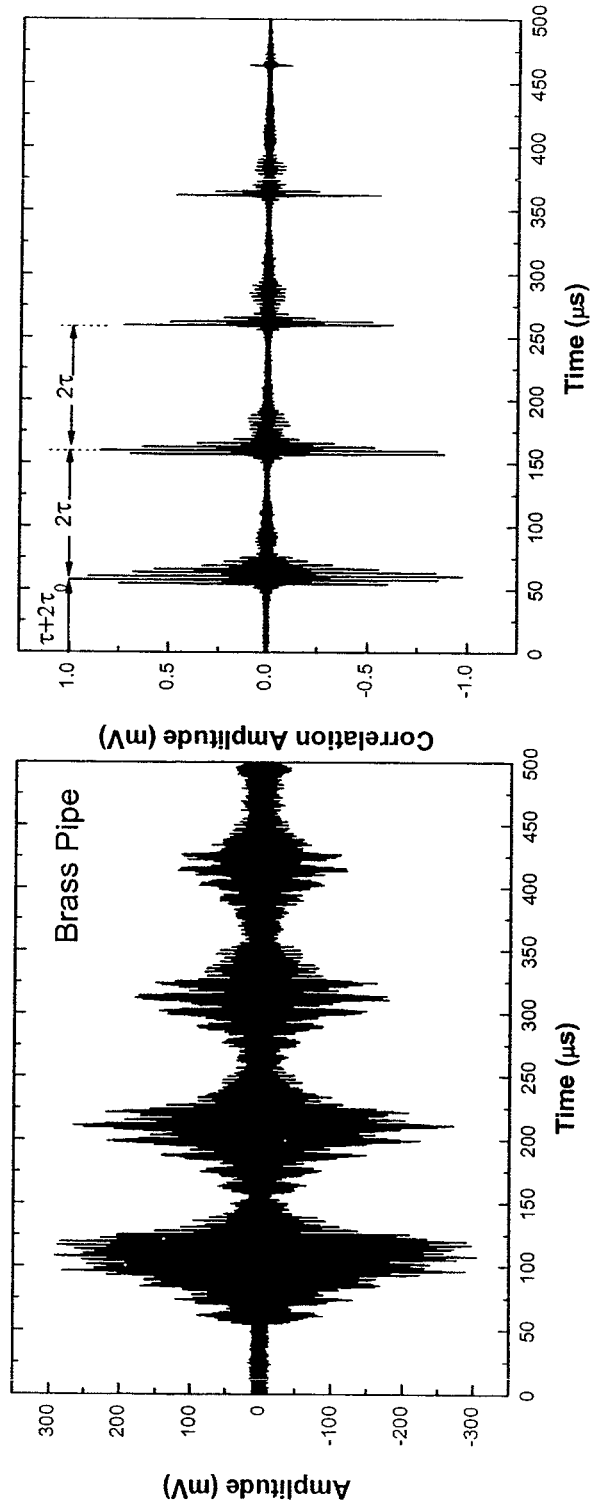

FIG. 6A is a graph of the signal detected by the receiver transducer from a water-filled brass pipe. Cross-correlation of this signal with the source signal from the transmitter transducer is shown in FIG. 6B, and illustrates significant pulse compression. It is straightforward to determine the time corresponding to first highest peak which corresponds to the total transit time through both walls ($\tau_o$) and through the fluid (τ). The time between any two consecutive peaks in FIG. 6B is predicted to be twice the time it takes the pulse to travel through the fluid (2τ) since the transit time through the walls is canceled in the difference. Thus, wall effects are removed, and an accurate measurement of the transit time through the fluid may be obtained. Since the inner diameter D of the pipe is known, the sound speed can be easily determined from the ratio D/τ. The height of the peaks from multiple reflections (transits through the fluid) may be used to extract the sound attenuation in the fluid. When the de-chirping and the cross-correlation methods are compared, the de-chirping method appears to be more immune to the amplitude variation of the chirp signal. For example, a square-wave chirp produces as well defined a de-chirped signal as the sine wave chirp produces. For cross-correlation, the quality of the result is degraded, because a square-wave consists of many higher harmonics. In the case of the dechirping, the frequency shift of the entire signal, point-by-point is observed, whereas in the case of the cross-correlation, the amplitude variation in the signal due to the presence of the higher harmonics and different phase of the harmonics, especially after multiple reflections in the wall, degrades the correlation results. Further processing is required to subtract out the higher harmonics to simplify the result. However, for high-quality sine wave chirps, both methods produce excellent results.

Figure 7A:
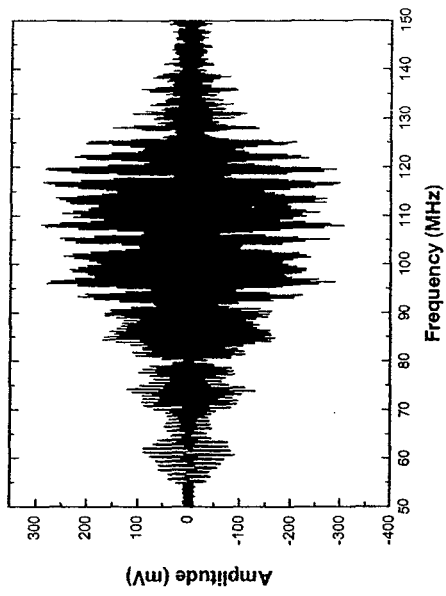
Figure 7C:
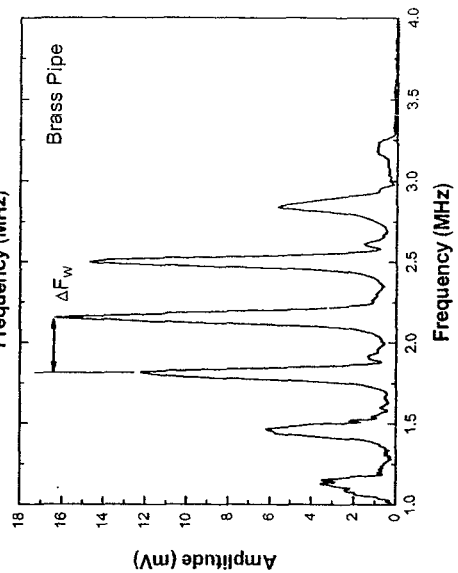
FIGS. 7C and 7D illustrate corresponding Fast Fourier Transforms of these signals, respectively.
Figure 7B:
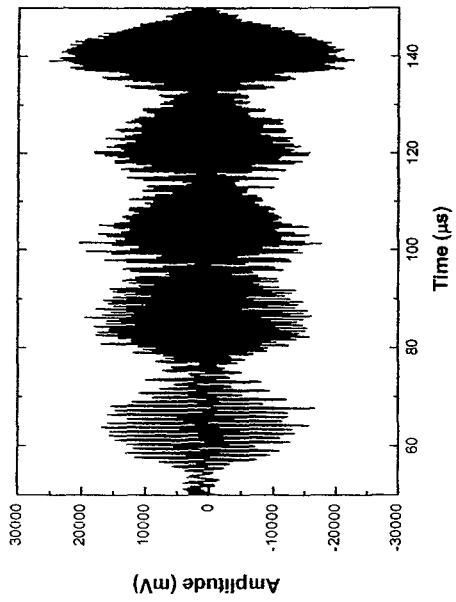
Figure 7D:
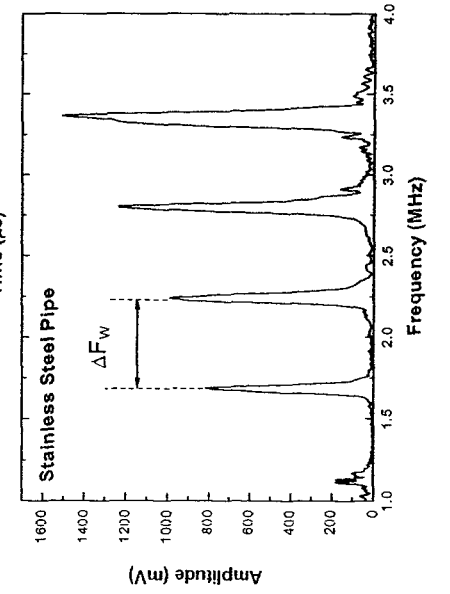

FIGS. 7A and 7B are graphs showing the first chirp burst received by the receiver transducer without the multiple echoes for a stainless steel and a brass pipe having identical dimensions, respectively, while FIGS. 7B and 7D show corresponding fast Fourier Transforms (FFTs) for these signals, respectively. This explains why the chirp signal received after going through the wall is amplitude modulated in the manner shown. The FFTs show multiple peaks within the 1-4 MHz range of the frequency chirp, and are the thickness mode resonances of the wall which determine the sound transmission characteristics of the wall. The peaks are equally spaced in frequency ($\Delta F_w$). The sound speed of the wall material and the wall thickness, d, are related through this difference frequency as:

$$\text{sound speed}(c_w) = 2 \times d \times \Delta F_w \quad (5)$$

Since the wall thickness of both steel and brass pipes were the same in the tests, the larger $\Delta F_w$ value of steel follows from the greater sound speed in steel as compared to that of brass.

If the sound speed of the wall material is known, thickness of the wall can be accurately determined.

Figure 8A:
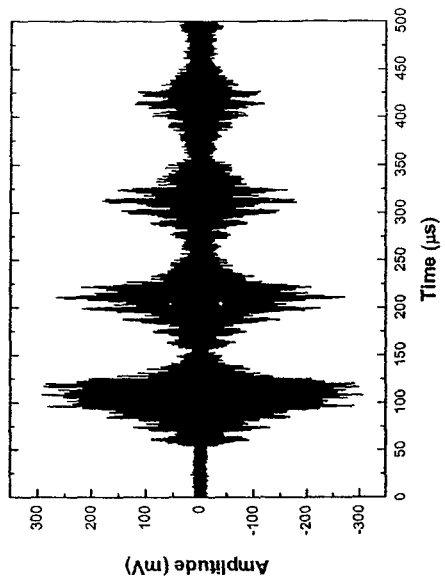
FIGS. 8A and 8B show the same received chirp signals from a brass pipe containing water, with FIG. 8B being recorded over a sufficient time span that the effects of recording multiple echoes can be separated, while corresponding Fast Fourier Transforms of the signals for FIGS. 8A and 8B are illustrated in FIGS. 8C and 8D, respectively.
Figure 8B:
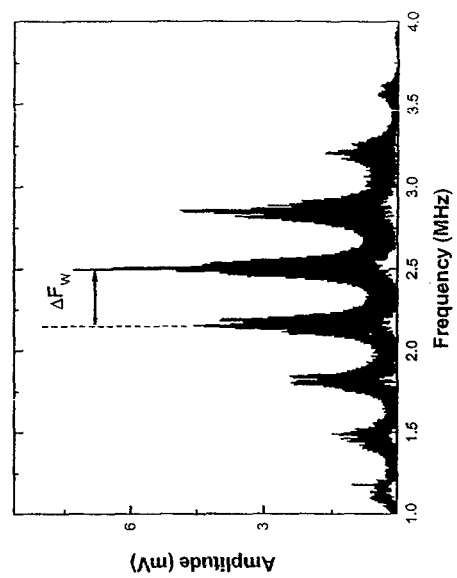
Figure 8C:
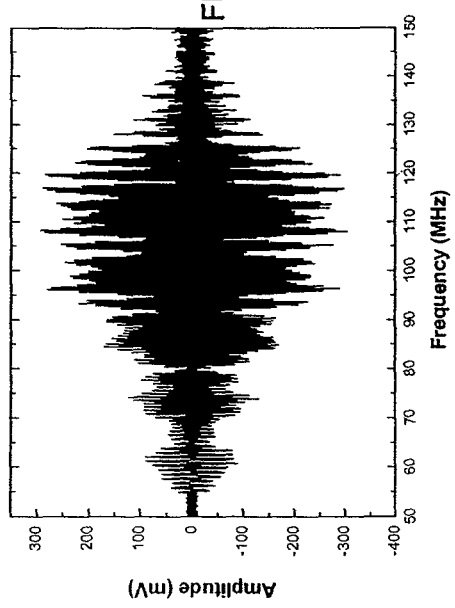
Figure 8D:
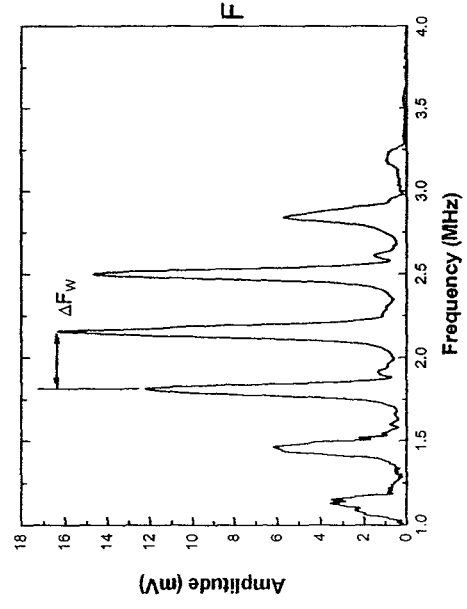

FIGS. 8A-8D show the effect of including multiple echoes in the reduction of the data. FIGS. 8A and 8B show the same received chirp signals for a brass pipe filled with water (Multiple echoes received by the receiver transducer imply that the signal has bounced back and forth through the liquid several times, and has had time to set up resonances, after which liquid resonances superimposed on the wall resonances are observed), with FIG. 8B being recorded over a sufficient time span that the effects due to recording multiple echoes can be separated from the wall effects. The corresponding FFTs of the signals for FIGS. 8A and 8B are illustrated in FIGS. 8C and 8D, respectively. In FIG. 8A, the sound has propagated only once through the pipe diameter and therefore no fluid resonances due to multiple reflections have been generated. The FFT in FIG. 8C principally illustrates the effect of the wall and attenuation due to the fluid. Fluid attenuation is reflected in the peak widths. In FIG. 8B, multiple reflections are included and the FFT now shows the resonances being set up in the fluid between the two transducers.

The liquid resonances can be separately studied from the wall resonances as illustrated in FIG. 9A where the FFT of received chirp signals, over a sufficient time period that permits recording multiple echoes for a brass pipe filled with water is shown. The wall resonance peaks are observed in FIG. 9A and the frequency difference between two neighboring walls peaks is displayed as $\Delta F_w$. The liquid resonance peaks appear as noise on this frequency scale and therefore a small region needs to be expanded to observe these resonances more clearly. FIGS. 8D and 9A are the same. FIG. 9B shows an expanded portion of the graph around 2.7 MHz in FIG. 9A that is enclosed with a dashed oval. A series of equally spaced peaks in frequency with a frequency spacing of $\Delta F_L$. In a similar manner to the sound speed in the walls of the pipe, the sound speed in fluid is given by:

$$\text{sound speed}(c_L) = 2 \times D \times \Delta F_L \quad (6)$$

Since the inner diameter of the pipe D is known, the sound speed in the liquid can be easily determined from the measurement of $\Delta F_L$. For the most accurate values of sound speed in liquids, measurements are made in the central region between any two consecutive wall peaks, which removes the influence of the wall on the liquid sound speed measurement.

Figure 10:
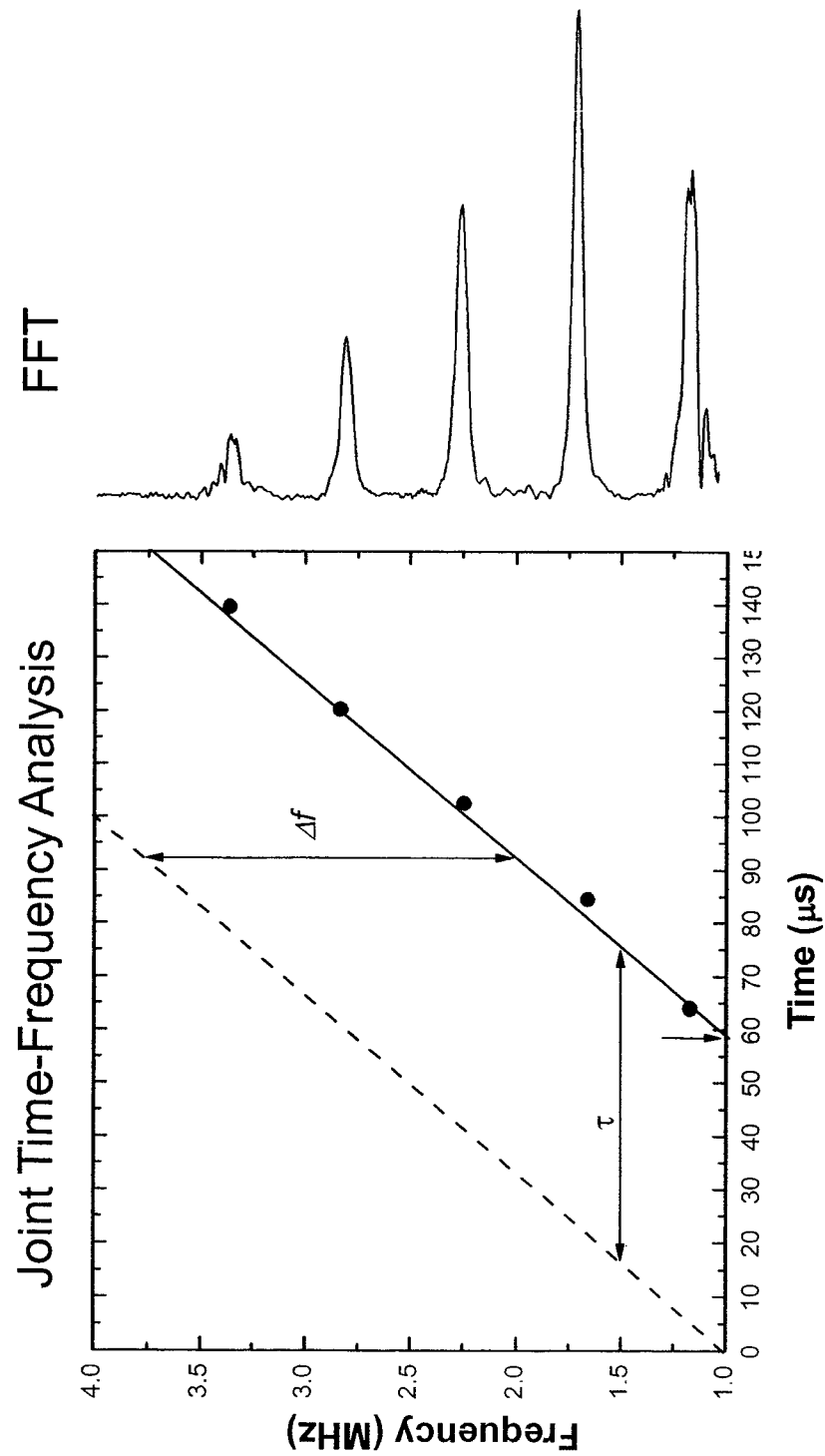
FIG. 10 is a graph illustrating two parallel state lines shifted in time, the first line representing the transmitted chirp between 1 and 4 MHz and having 100 µs duration starting at zero time, and the solid circles represent the peak positions in time and frequency of the various received wall peaks that modulate the sound transmission, with a least-squares fit made to this data, but constrained to the same slope as the transmitted chirp line being shown by the solid line, with the Fast Fourier Transform on the right of the graph being provided for comparison with the frequency transmission windows.

The Joint Time-Frequency Analysis (JTFA) of received chirped data is shown in FIG. 10 hereof. For comparison, the FFT of the received signal is shown on the right-hand side of the graph, which illustrates two parallel state lines shifted in time, the first line representing the transmitted chirp between 1 and 4 MHz and having 100 μs duration starting at zero time. The solid circles represent the peak positions in time and frequency of the various received wall peaks that modulate the sound transmission, each subsequent frequency peak arriving at a later time. A least squares fit made to this data, but constrained to the same slope as the transmitted chirp line is shown by the solid line. The intercept of this line at 1 MHz (chirp start frequency) on the time axis is the total transit time. Instead of JFTA, a continuous wavelet transform or other mathematical transform may be used to convert the data to time-frequency. This is a straightforward way to obtain the transit time from which the sound speed can be determined.

Figure 11B:
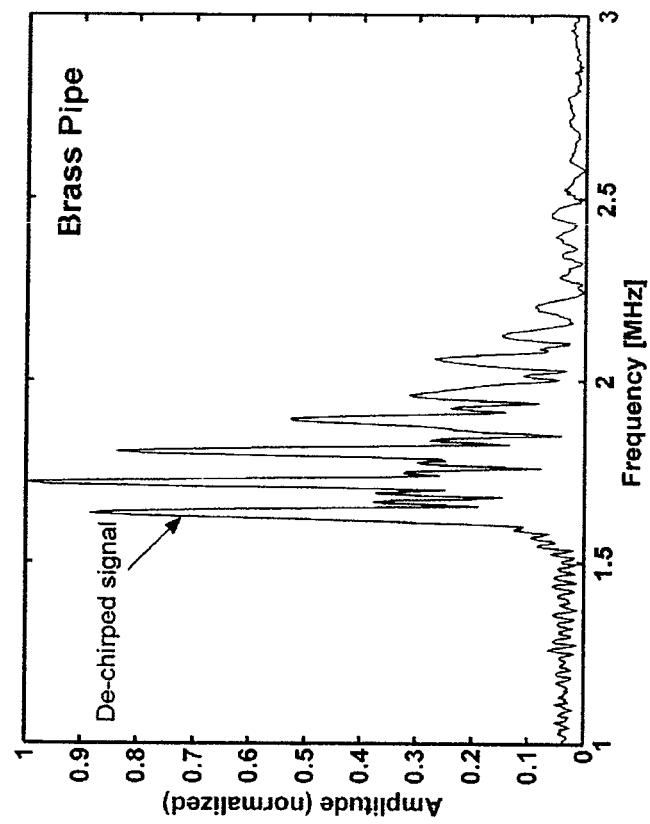
FIG. 11B is a graph of the Fast Fourier Transform of the product of the transmitted chirp and the received delayed chirp.
Figure 11A:
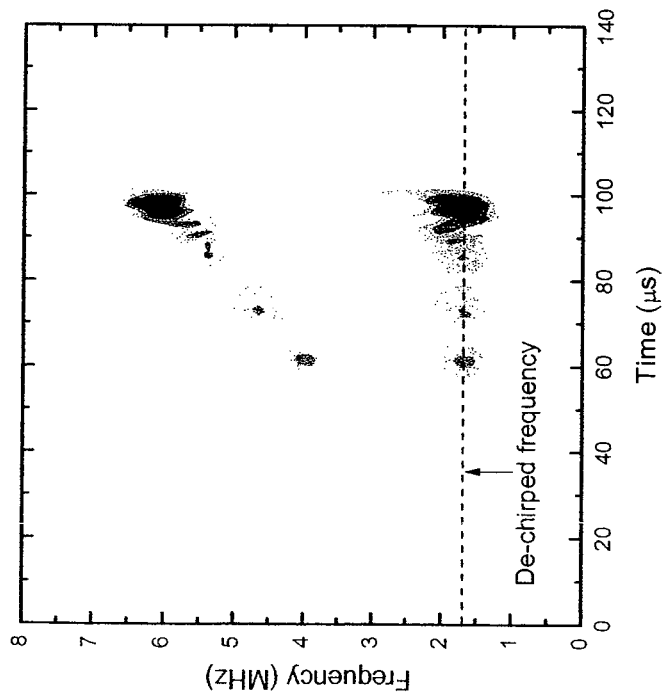

FIG. 11 illustrates the de-chirping technique described in FIGS. 4A and 4B and mathematically expressed in Eq. (4). The data shown in FIG. 11 is for a brass pipe containing water. First, the product of the source and received chirps are taken. If the delay is too great, such that there is no overlap or no significant overlap between the two signals, then one of the signals is translated in time until there is a reasonable degree (In the present situation, the duration of the chirp signal used is typically 100 μs, whereas the actual transmit time through the pipe and the liquid inside is approximately 50 μs. Therefore, if the transmitted and received signals are plotted in time from time zero and one signal is placed above the other one, there will be an overlap of the two signals. The final 50 μs of the transmit signal will overlap with the first 50 μs of the received signal. This kind of overlap is not always possible as in larger diameter pipes where the transmit time through the pipe may be longer than the duration of the transmit signal when the two signals will not overlap at all in time or overlap minimally. In such a situation, a certain amount of known delay time may be added to the transmit signal and shift it mathematically to make the two signals overlap better. Once the analysis is completed, the added time shift may be considered) of overlap, and the time shift is recorded for correcting the time.) of overlap, and the time shift is recorded for correcting the time. FIG. 11A shows the JTFA of the product data without any time shift since the two signals sufficiently overlapped (almost 50%). As predicted by Eq. 4, a fixed frequency is observed along with another, higher frequency component that varies with time. In an embodiment of the present invention, the fixed frequency de-chirped signal is of interest, and an average of all the peak values across the horizontal line provides the de-chirped frequency. In another embodiment, an FFT of the product is performed, which is illustrated in the plot shown FIG. 11B. The first peak in this case is the de-chirp frequency, and since the bandwidth and the duration of the chirp are known, the delay time can be obtained from the chirp rate and the frequency (FIGS. 4A and 4B, and Eq. 4). It is to be noted that the lowest frequency peak near 1.6 MHz has satellite peaks, which are due to multiple reflections in the wall as discussed in FIGS. 5A and 5B.

The measurements made from the five methods of analysis described hereinabove vary less than 0.02% for the observed data. For accurate determinations of the sound speed in liquids a single method or a combination of some or all of the five methods of analysis, may be used.

Once the sound speed is determined, it is possible to determine the composition of a 2-phase fluid, such as oil and water. The following Eqs. 7 and 8 are least-squares polynomial fits to experimental data of sound speed for crude oil ($c_o$) and process water ($c_w$) in m/s as a function of temperature, T, in °C.

$$c_w(T) = \Sigma_i A_{oi} T^i, \text{ and} \quad (7)$$

$$c_o(T) = \Sigma_i A_{wi} T^i. \quad (8)$$

For a particular sample pair, we have calibrated the polynomial coefficients as follows:

$$A_{w0}=1456.49, A_{w1}=3.39556, A_{w2}=-0.0116426, A_{w3}, A_{w4}, \ldots = 0$$

$$A_{o0}=1486.78, A_{o1}=-3.02556, A_{o2}=-0.008222, A_{o3}, A_{o4}, \ldots = 0$$

Further, the measured density ($\rho$) of a mixture of oil and water can be represented by a linear rule-of-mixtures in terms of the density of crude oil ($\rho_o$) and process water ($\rho_w$) approach as follows:

$$\rho = \Phi \rho_o + (1-\Phi)\rho_w, \quad (9)$$

where $\Phi$ is the volume fraction of the oil component. This simplified equation is straightforward to use in practice, but more accurate relationships may also be used. A similar linear rule can be applied to the compressibility ($\kappa$) of the mixture as:

$$\kappa = \Phi \kappa_o + (1-\Phi)\kappa_w, \quad (10)$$

where the individual compressibilities of the oil ($\kappa_o$) and water ($\kappa_w$) are used. The velocity of sound in the individual oil ($c_o$) and process water ($c_w$) mediums, as well as the mixture ($c$), are related to the respective densities and compressibilities by $$c^2=1/(\rho\kappa), c_o^2=1/(\rho_o\kappa_o) \text{ and } c_w^2=1/(\rho_w\kappa_w), \quad (11)$$

thus yielding $$\kappa_o/\kappa_w = o/(rw), \quad (12)$$

where $o=c^2/c_o^2$, $r=\rho_o/\rho_w$ and $w=c^2/c_w^2$. We can then write $$\kappa/\kappa_w = 1-\Phi[-o/(rw)] \quad (13)$$

By simple algebraic manipulations, Eq. (9) may be rewritten as $$\rho/\rho_w = 1-\Phi(1-r). \quad (14)$$

Upon multiplying equations (13) and (14), and applying (11), $$1/w = \{1-\Phi[1-o/(rw)]\} \times \{1-\Phi(1-r)\} \quad (15)$$

which, upon rearranging, takes the form of the quadratic equation $$(o-rw)(1-r)\Phi^2 + (2rw-o-r^2w)\Phi + r(1-w)\Phi = 0. \quad (16)$$

To obtain the oil-cut $\Phi$ (the fraction of oil in an oil-water mixture), the quadratic equation in (16) is solved, the root is selected such that $0 \leq \Phi \leq 1$.

To calibrate a system, it is useful to obtain a sample of the oil and the process water and then determine their sound speed dependence of temperature separately in a separate static cell. The system can be used for any composition of those two materials. Clearly, more sophisticated schemes may be devised once accurate measurements of sound speed are made. For example, sound attenuation is a strong function of temperature and fluid composition. Both sound speed and sound attenuation measurement can be combined to obtain a reliable measure of fluid composition.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for noninvasively determining the composition of a multiphase fluid comprising oil and water flowing through pipe having a wall and an outside surface, comprising:

generating an ultrasonic frequency chirp signal using a waveform generator, on a transmitting transducer in ultrasonic communication with the outside surface of said pipe;

receiving the generated frequency chirp signal on a receiving transducer in ultrasonic communication with the outside surface of said pipe diametrically opposed to the transmitting transducer after the chirp signal passes through said multiphase fluid, wherein an electrical signal is generated in response thereto;

receiving the electrical signal;

wherein the following steps are performed using a processor:

dechirping the frequency chirp by multiplying the received signal and the generated frequency chirp signal and obtaining the difference frequency from which the total transit time of the frequency chirp signal is determined;

determining the time delay of the frequency chirp signal in the wall of said pipe;

subtracting the time delay from the total transit time to determine the propagation time of the frequency chirp signal through said multiphase fluid, from which the composition of said multiphase fluid is determined; and storing the composition of said multiphase fluid for subsequent use.

2. The method of claim 1, wherein the frequency chirp signal comprises frequencies between about 100 kHz and approximately 10 MHz.

3. The method of claim 2, wherein the frequency chirp signal has a duration between about 10 μs and 10 ms.

4. The method of claim 3, wherein the duration of said frequency chirp signal is greater than the total transit time of the frequency chirp signal.

5. The method of claim 1, wherein the transmitting transducer and receiving transducer comprise piezoelectric transducers.

6. The method of claim 5, wherein the transmitting transducer and the receiving transducer are shaped so as to conform to the outside surface of said pipe.

7. The method of claim 1, further comprising the step of measuring the temperature of said multiphase fluid.

8. The method of claim 1, further comprising the steps of mathematically time shifting the propagation time of the frequency chirp signal such that the received signal and the generated frequency chirp signal overlap; and adding the time shifted propagation time to the total transit time of the frequency chirp signal.

9. The method of claim 1, wherein said step of determining the time delay of the frequency chirp signal in the wall of said pipe, comprises the steps of Fourier transforming the received electrical signal; and measuring the spacing between resonant peaks of the Fourier transformed received electrical signal from which the time delay is determined.

10. The method of claim 1, further comprising the steps of determining speed of sound in said oil as a function temperature; determining speed of sound in said water as a function temperature; generating an equation for expressing the speed of sound determination in oil and the speed of sound determination in water to the speed of sound in an unknown, two-phase fluid mixture of oil and water.

11. A method for noninvasively determining the composition of a multiphase fluid comprising oil and water flowing through pipe having a wall and an outside surface, comprising:

generating an ultrasonic frequency chirp signal using a waveform generator, on a transmitting transducer in ultrasonic communication with the outside surface of said pipe;

receiving the generated frequency chirp signal on a receiving transducer in ultrasonic communication with the outside surface of said pipe diametrically opposed to the transmitting transducer after the chirp signal passes through said multiphase fluid, wherein an electrical signal is generated in response thereto;

receiving the electrical signal;

wherein the following steps are performed using a processor:

cross-correlating the transmitted signal with the received signal, wherein cross-correlation peaks are generated;

selecting the highest peak which corresponds to the total transmit time of the frequency chirp signal;

determining the time delay of the frequency chirp signal in the wall of said pipe;

subtracting the time delay from the total transit time to determine the propagation time of the frequency chirp signal through said multiphase fluid, from which the composition of said multiphase fluid is determined; and storing the composition of said multiphase fluid for subsequent use.

12. The method of claim 11, wherein the frequency chirp signal comprises frequencies between about 100 kHz and approximately 10 MHz.

13. The method of claim 12, wherein the frequency chirp signal has a duration between about 10 μs and 16 ms.

14. The method of claim 11, wherein the transmitting transducer and receiving transducer comprise piezoelectric transducers.

15. The method of claim 14, wherein the transmitting transducer and the receiving transducer are shaped so as to conform to the outside surface of said pipe.

16. The method of claim 11, further comprising the step of measuring the temperature of said multiphase fluid.

17. The method of claim 11, wherein said step of determining the time delay of the frequency chirp signal in the wall of said pipe, comprises the steps of Fourier transforming the received electrical signal; and measuring the spacing between resonant peaks of the Fourier transformed received electrical signal from which the time delay is determined.

18. The method of claim 11, further comprising the steps of determining speed of sound in said oil as a function temperature; determining speed of sound in said water as a function temperature; generating an equation for expressing the speed of sound determination in oil and the speed of sound determination in water to the speed of sound in an unknown, two-phase fluid mixture of oil and water.

19. A method for noninvasively determining the composition of a multiphase fluid comprising oil and water flowing through pipe having a wall and an outside surface, comprising:

generating an ultrasonic frequency chirp signal using a waveform generator, on a transmitting transducer in ultrasonic communication with the outside surface of said pipe;

receiving the generated frequency chirp signal on a receiving transducer in ultrasonic communication with the outside surface of said pipe diametrically opposed to the transmitting transducer after the chirp signal passes through said multiphase fluid, wherein an electrical signal is generated in response thereto;

receiving the electrical signal;

wherein the following steps are performed using a processor:

cross-correlating the transmitted signal with the received signal, wherein cross-correlation peaks are generated;

determining the time between consecutive peaks, wherein the determined time is twice the travel time through said multiphase fluid, from which the composition of said multiphase fluid is determined; and storing the composition of said multiphase fluid for subsequent use.

20. The method of claim 19, wherein the frequency chirp signal comprises frequencies between about 100 kHz and approximately 10 MHz.

21. The method of claim 20, wherein the frequency chirp signal has a duration between about 10 μs and 10 ms.

22. The method of claim 19, wherein the transmitting transducer and receiving transducer comprise piezoelectric transducers.

23. The method of claim 22, wherein the transmitting transducer and the receiving transducer are shaped so as to conform to the outside surface of said pipe.

24. The method of claim 19, further comprising the step of measuring the temperature of said multiphase fluid.

25. The method of claim 19, further comprising the steps of determining speed of sound in said oil as a function temperature; determining speed of sound in said water as a function temperature; generating an equation for expressing the speed of sound determination in oil and the speed of sound determination in water to the speed of sound in an unknown, two-phase fluid mixture of oil and water.

26. The method of claim 19, further comprising the steps of: Fourier transforming the cross-correlation peaks; expanding the resulting spectrum in the frequency domain to obtain equidistant peaks corresponding to liquid resonances; determining the frequency spacing between adjacent peaks; and averaging over multiple peak spacings from which the speed of sound in said multiphase fluid is determined.

27. A method for noninvasively determining the composition of a multiphase fluid comprising oil and water flowing through pipe having a wall and an outside surface, comprising:
  generating an ultrasonic frequency chirp signal having a duration shorter than the time the frequency chirp takes to pass through said multiphase fluid using a waveform generator, on a transmitting transducer in ultrasonic communication with the outside surface of said pipe;
  receiving the generated frequency chirp signal on a receiving transducer in ultrasonic communication with the outside surface of said pipe diametrically opposed to the transmitting transducer after the chirp signal passes through said multiphase fluid, wherein an electrical signal is generated in response thereto;
  receiving the electrical signal;
  wherein the following steps are performed using a processor;
  transforming the electrical signal using a Short Time Fourier Transform, whereby a plot of the frequency variation of the received frequency chirp as a function of time is generated, and amplitude modulations due to wall resonances appear as individual localized peaks falling on a straight line having a slope;
  performing a least-squares fit of the individual localized peaks with a straight line having the slope;
  determining the intercept on the time axis from which the total transit three is determined;
  determining the time delay of the frequency chirp signal in the wall of said pipe;
  subtracting the time delay from the total transit time to determine the propagation time of the frequency chirp signal through said multiphase fluid, from which the composition of said multiphase fluid is determined; and
  storing the composition of said multiphase fluid for subsequent use.

28. The method of claim 27, wherein the frequency chirp signal comprises frequencies between about 100 kHz and approximately 10 MHz.

29. The method of claim 28, wherein the frequency chirp signal has a duration between about 10 μs and 10 ms.

30. The method of claim 27, wherein the transmitting transducer and receiving transducer comprise piezoelectric transducers.

31. The method of claim 30, wherein the transmitting transducer and the receiving transducer are shaped so as to conform to the outside surface of said pipe.

32. The method of claim 27, further comprising the step of measuring the temperature of said multiphase fluid.

33. The method of claim 27, wherein said step of determining the time delay of the frequency chirp signal in the wall of said pipe, comprises the steps of Fourier transforming the received electrical signal; and measuring the spacing between resonant peaks of the Fourier transformed received electrical signal from which the time delay is determined.

34. The method of claim 27, further comprising the steps of determining speed of sound in said oil as a function temperature; determining speed of sound in said water as a function temperature; generating an equation for expressing the speed of sound determination in oil and the speed of sound determination in water to the speed of sound in an unknown, two-phase fluid mixture of oil and water.

* * * * *